(12) United States Patent
Sabol et al.

(10) Patent No.: US 7,618,712 B2
(45) Date of Patent: *Nov. 17, 2009

(54) APPARATUS AND METHOD OF DETECTING WEAR IN AN ABRADABLE COATING SYSTEM

(75) Inventors: Stephen M. Sabol, Orlando, FL (US); Ramesh Subramanian, Oviedo, FL (US); Anand A. Kulkarni, Orlando, FL (US)

(73) Assignee: Siemens Energy, Inc., Orlando, FL (US)

(*) Notice: Subject to any disclaimer, the term of this patent is extended or adjusted under 35 U.S.C. 154(b) by 675 days.

This patent is subject to a terminal disclaimer.

(21) Appl. No.: 11/269,044

(22) Filed: Nov. 8, 2005

(65) Prior Publication Data

US 2006/0056960 A1    Mar. 16, 2006

Related U.S. Application Data

(63) Continuation-in-part of application No. 11/122,566, filed on May 5, 2005, and a continuation-in-part of application No. 11/018,816, filed on Dec. 20, 2004, now Pat. No. 7,270,890, which is a continuation-in-part of application No. 10/252,236, filed on Sep. 23, 2002, now Pat. No. 6,838,157.

(60) Provisional application No. 60/581,662, filed on Jun. 21, 2004.

(51) Int. Cl.
   *B32B 9/00*   (2006.01)
(52) U.S. Cl. .................. 428/469; 428/472; 428/210
(58) Field of Classification Search .................. None
   See application file for complete search history.

(56) References Cited

U.S. PATENT DOCUMENTS 4,063,167 A    12/1977    Duly (Continued)

OTHER PUBLICATIONS

L. Lü, J.Y.H. Fuh, Y.S. Wong; "Laser-Induced Materials and Processes for Rapid Prototyping"; 2001; pp. 143-186; Chapter 6 — Metal-Based System Via Laser Melting; Kluwer Academic Publishers; Boston, MA.

(Continued)

*Primary Examiner*—Timothy M Speer

(57) ABSTRACT

A component for use in a combustion turbine (10) is provided that includes a substrate (212) and an abradable coating system (216) deposited on the substrate (212). A planar proximity sensor (250) may be deposited beneath a surface of the abradable coating system (216) having circuitry (252) configured to detect intrusion of an object (282) into the abradable coating system (216). A least one connector (52) may be provided in electrical communication with the planar proximity sensor (250) for routing a data signal from the planar proximity sensor (250) to a termination location (59). A plurality of trenches (142) may be formed at respective different depths below the surface of the abradable coating system (216) with a planar proximity sensor (250) deposited within each of the plurality of trenches (142). A processing module (34) may be programmed for receiving data from the planar proximity sensor (250) and calculating a clearance between a row of blades (18,19) within a combustion turbine and the planar proximity sensor (250). The processing module (34) may control a clearance between the row of blades (18) and a ring segment (284) based on data received from the planar proximity sensors (250).

10 Claims, 9 Drawing Sheets

U.S. PATENT DOCUMENTS

| | | | |
|---|---|---|---|
| 4,546,652 A | 10/1985 | Virkar et al. |
| 4,970,670 A | 11/1990 | Twerdochlib |
| 5,119,036 A | 6/1992 | Rickards et al. |
| 5,440,300 A | 8/1995 | Spillman, Jr. |
| 5,760,593 A | 6/1998 | Lawrence et al. |
| 5,797,414 A | 8/1998 | Sirovich et al. |
| 5,867,302 A | 2/1999 | Fleming |
| 5,952,836 A | 9/1999 | Haake |
| 5,969,260 A | 10/1999 | Belk et al. |
| 5,970,393 A | 10/1999 | Khorrami et al. |
| 6,034,296 A | 3/2000 | Elvin et al. |
| 6,043,644 A | 3/2000 | de Coulon et al. |
| 6,109,783 A | 8/2000 | Dobler et al. |
| 6,197,424 B1 | 3/2001 | Morrison et al. |
| 6,251,488 B1 | 6/2001 | Miller et al. |
| 6,262,550 B1 | 7/2001 | Kliman et al. |
| 6,273,671 B1 | 8/2001 | Ress, Jr. |
| 6,301,572 B1 | 10/2001 | Harrison |
| 6,331,823 B1 | 12/2001 | El-Ibiary |
| 6,343,251 B1 | 1/2002 | Herron et al. |
| 6,512,379 B2 | 1/2003 | Harrold et al. |
| 6,516,671 B2 | 2/2003 | Romo et al. |
| 6,523,383 B2 | 2/2003 | Joki et al. |
| 6,532,412 B2 | 3/2003 | Adibhatla et al. |
| 6,556,956 B1 | 4/2003 | Hunt |
| 6,576,861 B2 | 6/2003 | Sampath et al. |
| 6,591,182 B1 | 7/2003 | Cece et al. |
| 6,667,725 B1 | 12/2003 | Simons et al. |
| 6,670,046 B1 | 12/2003 | Xia |
| 6,717,420 B2 | 4/2004 | Eyraud et al. |
| 6,723,379 B2 | 4/2004 | Stark |
| 6,735,549 B2 | 5/2004 | Ridolfo |
| 6,756,908 B2 | 6/2004 | Gass et al. |
| 6,760,689 B2 | 7/2004 | Follin et al. |
| 6,796,187 B2 | 9/2004 | Srinivasan et al. |
| 6,816,817 B1 | 11/2004 | Retlich et al. |
| 6,822,440 B2 | 11/2004 | Machul |
| 6,831,555 B1 | 12/2004 | Miller et al. |
| 6,838,157 B2 | 1/2005 | Subramanian |
| 7,270,890 B2 * | 9/2007 | Sabol et al. | 428/632 |
| 7,368,827 B2 * | 5/2008 | Kulkarni et al. | 290/52 |
| 2002/0170890 A1 | 11/2002 | Keicher et al. |

OTHER PUBLICATIONS

Alberto Piqué, Douglas B. Chrisey; "Direct-Write Technologies for Rapid Prototyping Applications: Sensors, Electronics, and Integrated Power Sources"; 2002; pp. 261-302; Chapter 9—Direct-Write Thermal Spraying of Multilayer Electronics and Sensor Structures; Academic Press; San Diego, CA.

V.K. Varadan and V.V. Varadan; "Microsensors, Microelectromechanical Systems (MEMS), and Electronics for Smart Structures and Systems"; 2000; pp. 953-972; Smart Mater. Struct. 9; IOP Publishing Ltd.; UK.

* cited by examiner

APPARATUS AND METHOD OF DETECTING WEAR IN AN ABRADABLE COATING SYSTEM

CROSS REFERENCE TO RELATED APPLICATIONS

This application is a continuation-in-part of U.S. patent application Ser. No. 11/122,566 filed May 5, 2005, which claims the benefit of Provisional Patent Application No. 60/581,662 filed on Jun. 21, 2004, which is also a continuation-in-part of U.S. patent application Ser. No. 11/018,816 filed Dec. 20, 2004, now U.S. Pat. No. 7,270,890 which is a continuation-in-part of U.S. patent application Ser. No. 10/252,236 filed Sep. 23, 2002, now U.S. Pat. No. 6,838,157 all of which are incorporated herein by reference.

FIELD OF THE INVENTION

The present invention relates generally to monitoring parameters of operating environments and particularly to an apparatus and method of determining wear behavior of an abradable coating system deposited on components within an operating environment such as a gas turbine engine.

BACKGROUND OF THE INVENTION

Gas combustion turbines are used for a variety of applications such as driving an electric generator in a power generating plant or propelling a ship or an aircraft. Firing temperatures in modern gas turbine engines continue to increase in response to the demand for higher efficiency engines. Superalloy materials have been developed to withstand the corrosive high temperature environment that exists within a gas turbine engine. However, even superalloy materials are not able to withstand extended exposure to the hot combustion gas of a current generation gas turbine engine without some form of cooling and/or thermal insulation.

Thermal barrier coatings are widely used for protecting various hot gas path components of a gas turbine engine. The reliability of such coatings is critical to the overall reliability of the machine. The design limits of such coatings are primarily determined by laboratory data. However, validation of thermal barrier coating behavior when subjected to the stresses and temperatures of the actual gas turbine environment is essential for a better understanding of the coating limitations. Such real world operating environment data is very difficult to obtain, particularly for components that move during the operation of the engine, such as the rotating blades of the turbine.

Despite the extreme sophistication of modern turbine engines, such as gas turbines for generating electrical power or aircraft engines for commercial and military use, designers and operators have very little information regarding the internal status of the turbine engine components during operation. This is due to the harsh operating conditions, which have prevented the use of traditional sensors for collecting reliable information of critical engine components.

Many current turbines are equipped with sensors capable of limited functions such as exhaust gas-path temperature measurements, flame detection and basic turbine operating conditions. Based on this information, turbine operators such as utility companies operate engines in a passive mode, in which maintenance is scheduled based on prior histories of similar engines. Engine rebuilds and routine maintenance are performed in the absence of a prior knowledge of the remaining or already utilized life of individual components. The lack of specific component information makes early failure detection very difficult, often with the consequence of catastrophic engine failure due to abrupt part failure. This results in inefficient utilization, unnecessary downtime and an enormous increase in operating cost.

Currently, the gas turbine industry approach is to depend on the measurement of gas path temperature, which is related back to specific component problems based on experience and history regarding a class of engines. This approach is highly subjective and only allows for determining already severe situations with an engine. It does not provide indications of impending damage or insight into the progression of events leading up to and causing engine damage due to component degradation or failure.

The instrumentation of a component such as a blade or vane within a steam turbine typically includes placing wire leads on the balance wheel, which continue on to the blade airfoil. The wire leads are typically held together by an epoxy. These wires are routed from within the component to the turbine casing. The pressure boundary of a component may be breached to introduce a sensor such as a thermocouple and a braze is back filled to hold the thermocouple in place. Each thermocouple sensor has wire leads coming out of the component that are connected back to a diagnostic unit. Instrumenting a plurality of components of a turbine in this manner results in an extensive network of wires just for monitoring the single operating condition of temperature. Instrumenting components using this technique is expensive, which is a barrier to instrumenting a large number of components within a single turbine. Further, the wire leads and data transfer is frequently poor, which can result in costly repairs and flawed data analysis.

Using thermocouples for temperature measurements in the gas path of a turbine may be disadvantageous because it only provides feedback to an operator that a temperature change has occurred in the gas path. It does not provide any indication as to why the temperature change has occurred. For diagnosing problems with blades or vanes based on a measured temperature change, there has to be an historical correlation between the measured temperature differential and the specific problem, such as a hole in a vane. This correlation is difficult and time consuming to derive to within a reasonable degree of certainty and needs to be done on an engine-by-engine basis taking into account turbine operation conditions. When a temperature differential is measured, it is difficult, if not impossible, to predict what the problem is or where it is located. Consequently, the turbine must typically be shut down and inspected to determine the scope of repair, replacement or other maintenance to be performed.

In any application, combustion turbines are routinely subject to various maintenance procedures as part of their normal operation. Diagnostic monitoring systems for gas turbines commonly include performance monitoring equipment that collects relevant trend and fault data used for diagnostic trending. In diagnostic trend analysis, certain process data (such as exhaust gas temperature, fuel flow, rotor speed and the like) that are indicative of overall gas turbine performance and/or condition are compared to a parametric baseline for the gas turbine. Any divergence of the raw trend data from the parametric baseline may be indicative of a present or future condition that requires maintenance. Such diagnostic monitoring systems can only predict or estimate specific component conditions and do not collect data from or provide any analysis with respect to the actual condition of a specific component itself.

In this respect, conventional methods of predicting component failure for gas turbines and of scheduling maintenance have not been entirely accurate or optimized. The traditional "duty cycle" used for predictive maintenance does not reflect real operational conditions, especially off-design operations. The actual life of specific components of a gas turbine depends strongly on the actual usage of that gas turbine and the specific components within the turbine.

For example, elevated temperatures and stresses within the turbine, and aggressive environmental conditions may cause excessive wear on components in the turbine beyond that predicted with the standard design duty cycle. Off-design operating conditions, which are often experienced by industrial gas turbines, are not reflected by the standard duty cycles. The actual life of components in the gas turbine may be substantially less than that predicted by the design duty cycle. Alternatively, if more favorable conditions are experienced by an actual gas turbine than are reflected in the design duty cycle, the actual component life may last substantially longer than that predicted by maintenance schedules based on the design duty cycle. In either event, the standard design duty cycle model for predicting preventive maintenance does not reliably indicate the actual wear and tear experienced by gas turbine components.

Known techniques for predicting maintenance and component replacement rely on skilled technicians to acquire or interpret data regarding the operation of a combustion turbine. Such techniques are subject to varying interpretations of that data by technicians. Technicians may manually evaluate the operational logs and/or data collected from gas turbines. Technicians, for example, may evaluate start and stop times and power settings to determine how many duty cycles had been experienced by the gas turbine, their frequency, period and other factors. In addition, if the data log of a gas turbine indicated that extraordinary conditions existed, such as excessive temperatures or stresses, the technicians may apply "maintenance factors" to quantify the severity of these off-design operational conditions.

None of these techniques provide accurate information with respect to the actual condition of a specific component or component coating, which may lead to unnecessary repair, replacement or maintenance being performed causing a significant increase in operating costs.

DETAILED DESCRIPTION OF THE INVENTION

Embodiments of the present invention use sensors, such as a planar proximity sensor, embedded within coatings, such as an abradable coating system, or installed on or within a surface of a component to determine the wear behavior of the coating or component when contacted by another component. Abradable coating systems may be used for gas path clearance control, which influences power output and efficiency of a gas turbine such as the exemplary combustion turbine of FIG. 1. The abradable coating system abrades when contacted by another component, such as a plurality of rotating blades 18 secured to a rotatable central shaft 20 mounted within turbine 16.

Figure 1:
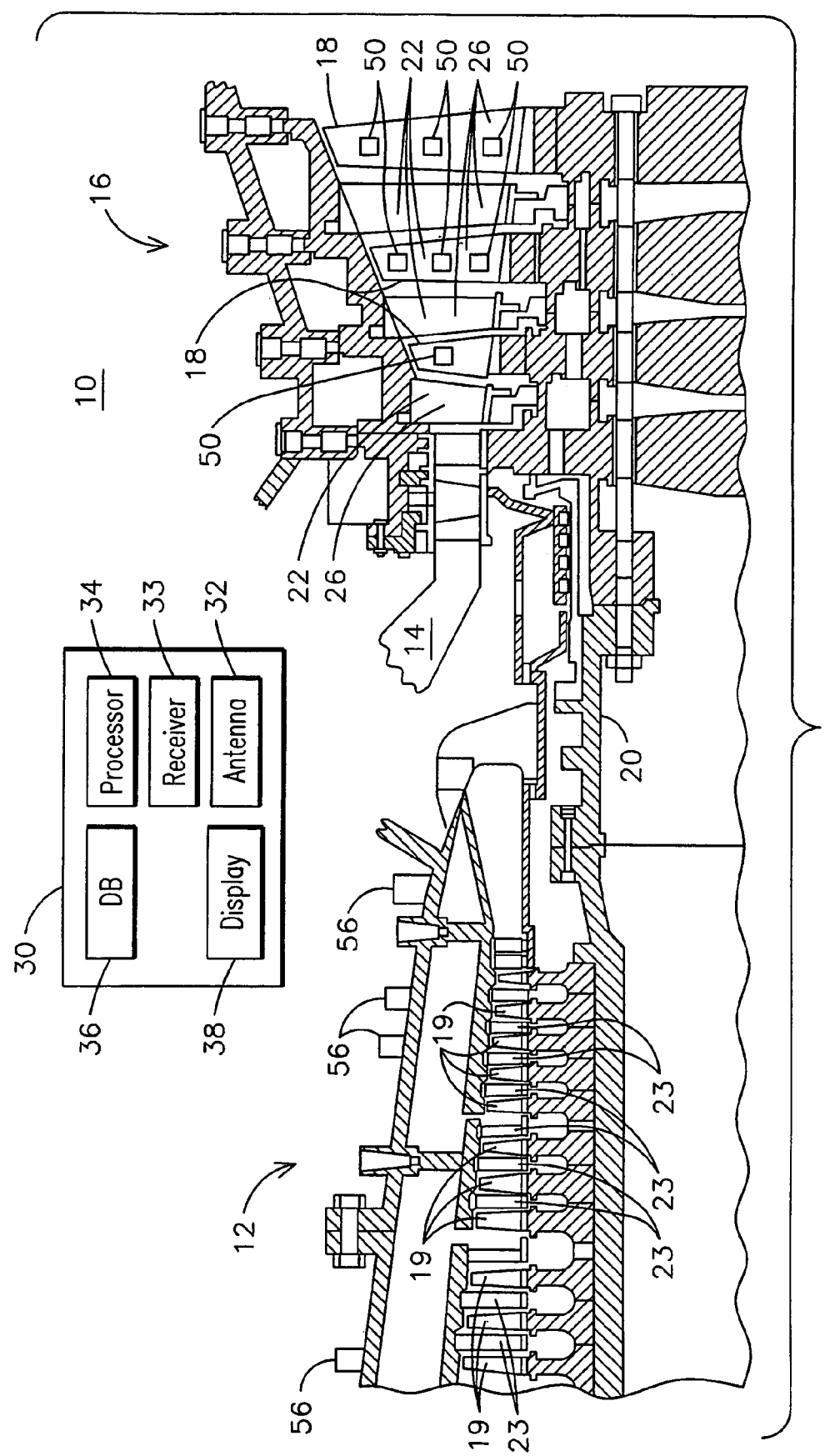
FIG. 1 is a cross sectional view of an exemplary combustion turbine with which embodiments of the invention may be used and an exemplary monitoring and control system for collecting and analyzing component data from the combustion.

FIG. 1 illustrates an exemplary combustion turbine 10 such as a gas turbine used for generating electricity as will be recognized by those skilled in the art. Embodiments of the invention may be used with combustion turbine 10 or in numerous other operating environments and for various purposes as will be recognized by those skilled in the art. For example, embodiments may be used in aircraft engines, monitoring temperature and heat flux in boilers, heat exchangers and exhaust stacks; determining insulation performance and degradation; determining pipe fouling; and evaluating vibrating component health. Embodiments may be used in the automotive industry for monitoring combustion chamber conditions, rotating components such as crankshaft, cams, transmissions and differentials, and determining suspension and frame integrity for heavy-duty vehicles. Embodiments may also be used in measuring strain and heat flux in tanks, portable and other equipment operating in dessert, wet, and/or high temperature configurations.

Returning to FIG. 1, combustion turbine 10 includes a compressor 12, at least one combustor 14 (broken away) and a turbine 16. Compressor 12, combustor 14 and turbine 16 are sometimes referred to collectively as a gas turbine engine. Turbine 16 includes a plurality of rotating blades 18, secured to a rotatable central shaft 20. A plurality of stationary vanes 22 are positioned between blades 18, with vanes 22 being dimensioned and configured to guide air over blades 18. Blades 18 and vanes 22 will typically be made from nickel-cobalt, and may be coated with a thermal barrier coating 26, such as yttria-stabilized zirconia. Similarly, compressor 12 includes a plurality of rotating blades 19 positioned between respective vanes 23.

In use, air is drawn in through compressor 12, where it is compressed and driven towards combustor 14. Combustor 14 mixes the air with fuel and ignites it thereby forming a working gas. This working gas will typically be above 1300° C. This gas expands through turbine 16, being guided across blades 18 by vanes 22. As the gas passes through turbine 16, it rotates blades 18 and shaft 20, thereby transmitting usable mechanical work through shaft 20. Combustion turbine 10 may also include a cooling system (not shown), dimensioned and configured to supply a coolant, for example steam or compressed air, to blades 18 and vanes 22.

The environment wherein blades 18 and vanes 22 operate is subject to high operating temperatures and is particularly harsh, which may result in serious deterioration of blades 18 and vanes 22. This is especially likely if the thermal barrier coating 26 should spall or otherwise deteriorate. Embodiments of the invention are advantageous because they allow components to be configured for transmitting data indicative of a component's condition during operation of combustion turbine 10. Blades 18, 19, vanes 22, 23, and coatings 26, for example, may be configured for transmitting component specific data that may be directly monitored to determine the respective condition of each component during operation and to develop predictive maintenance schedules.

FIG. 1 also illustrates a schematic of an exemplary monitoring and control system 30 that may be used in accordance with various aspects of the present invention. System 30 may include an antenna 32, a receiver 33, a processor or CPU 34, a database 36 and a display 38. Processor 34, database 36 and display 38 may be conventional components and antenna 32 and receiver 33 may have performance specifications that are a function of various embodiments of the invention. For example, antenna 32 and receiver 33 may be selected for receiving wireless telemetry data transmitted from a plurality of transmitters deployed in various locations throughout combustion turbine 10 as more fully described below.

Embodiments of the present invention allow for a plurality of sensors to be embedded within the respective coatings of a plurality of components within combustion turbine 10. Alternate embodiments allow for the sensors to be surface mounted or deposited to components, especially those contained in areas where components do not require a barrier coating such as the compressor. Exemplary embodiments of sensors may be used to provide data to system 30 with respect to physical characteristics of a component and/or properties of a component's coating as well as other component or coating specific information.

For example, exemplary sensors may be used to detect wear between two components, measure heat flux across a component's coating, detect spalling of a coating, measure strain across an area of a component or determine crack formation within a component or coating. Those skilled in the art will recognize other properties and/or characteristics of a component or component coating that may be measured and/or detected in accordance with aspects of the invention.

It will be appreciated that aspects of the invention allow for various sensor configurations to be embedded within a barrier coating such as a barrier coating 26 of blades 18 or vanes 22 of turbine 16. U.S. Pat. No. 6,838,157, which is specifically incorporated herein by reference, describes various embodiments of methods for instrumenting gas turbine components, such as blades 18 and vanes 22 that may be utilized for depositing sensors in accordance with aspects of the present invention. This patent discloses various methods of forming trenches in a barrier coating, forming a sensor in the coating and depositing a backfill material in the trench over the coating. Embodiments of those methods and components may be used to form smart components as disclosed herein.

U.S. Pat. No. 6,576,861, which is specifically incorporated herein by reference, discloses a method and apparatus that may be used to deposit embodiments of sensors and sensor connectors with transmitters in accordance with aspects of the present invention. In this respect, methods and apparatus disclosed therein may be used for the patterning of fine sensor and/or connector features of between about 100 microns and 500 microns without the need of using masks. Multilayer electrical circuits and sensors may be formed by depositing features using conductive materials, resistive materials, dielectric materials, insulative materials and other application specific materials. It will be appreciated that other methods may be used to deposit multilayer electrical circuits and sensors in accordance with aspects of the invention. For example, thermal spraying, vapor deposition, laser sintering and curing deposits of material sprayed at lower temperatures may be used as well as other suitable techniques recognized by those skilled in the art.

Embodiments of the invention allow for a plurality of sensors 50 to be deployed in numerous places within combustion turbine 10 for monitoring component-specific or coating-specific conditions as well as collecting other data with respect to the operation or performance of combustion turbine 10. For example, FIG. 1 illustrates that one or more sensors 50 may be embedded within respective barrier coatings 26 of one or more blades 18 of turbine 16. It will be appreciated that sensors 50 may be embedded within barrier coatings of other components with turbine 16 for which component-specific and/or coating-specific data is to be acquired.

Figure 2:
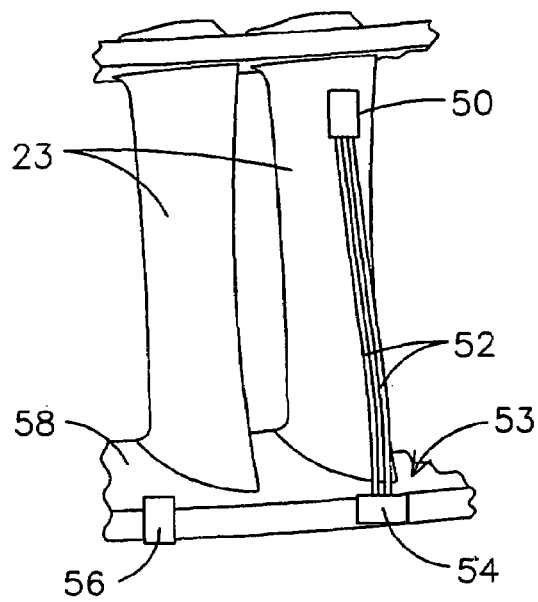
FIG. 2 a perspective view of an exemplary combustion turbine vane equipped with an exemplary embodiment of the present invention.

FIG. 2 illustrates a pair of vanes 23 removed from compressor 12 with one vane having a sensor 50 mounted or connected with vane 23 for detecting a condition of vane 23. A connector 52 may be provided for as a means for routing a data signal from sensor 50 to a transmitter 54 configured for wirelessly transmitting the data signal to a transceiver 56. Connector 52 may be one or a plurality of electrical leads for conducting a signal from sensor 50 to a surface mounted transmitter 54. Alternate embodiments allow for various types of connectors 52 to be used as a means for routing a data signal from sensor 50 to transmitter 54, depending on the specific application. For example, one or a plurality of fiber optic connectors may be used for routing a signal using single or varying wavelengths of light.

Embodiments allow for transmitters 54 to be multi-channel and have various specifications depending on their location within a casing of combustion turbine 10. Transmitters 54 may be configured to function within the compressor 12 casing subject to operating temperatures of between about 80° C. to 120° C. They may also be configured to function within the turbine 12 casing subject to operating temperatures of between about 300° C. to 350° C. of higher, and be resistant to oxidative exposure.

Figure 3:
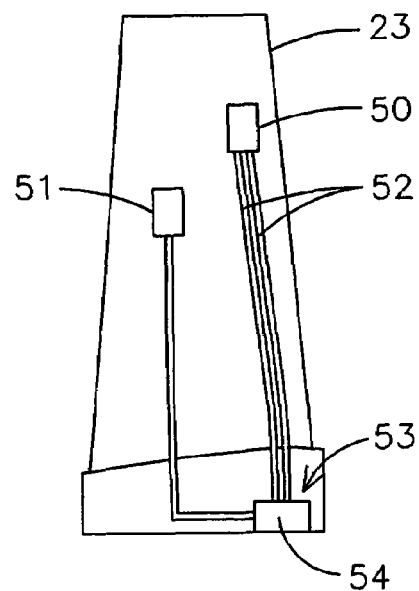
FIG. 3 is a schematic view of a vane of FIG. 2.

FIG. 3 illustrates a schematic plan view of compressor vane 23 having sensor 50 connected therewith and connector 52 connecting sensor 50 with transmitter 54. A power source 51 may be provided, such as an appropriately sized battery for powering transmitter 54. In alternate embodiments transmitter 54 may be located remotely from vane 23 and powered from an external power source. Transmitter 54 may receive signals from sensor 50 via connector 52 that are subsequently wirelessly transmitted to transceiver 56. Transceiver 56 may be mounted on hub 58 or on a surface external to compressor 12 such as the exemplary locations shown in FIG. 1. Transceiver 56 may be mounted in various locations provided it is within sufficient proximity to transmitter 54 to receive a wireless data transmission, such as an RF signal from transmitter 54. Transceiver 56 may transmit the RF signal to antenna 32 of system 30 where the signal may be processed for monitoring the condition of compressor vane 23.

With respect to FIGS. 2 and 3, one or more sensors 50 may be connected with one or more compressor vanes 23 by fabricating sensor 50 directly onto a surface of vane 23. Connector 52 may be deposited directly onto a surface of vane 23. In alternate embodiments a trench or recess may be formed within a surface of vane 23 that is sized for receiving a deposited sensor 50 and connector 52. Sensor 50 and connector 52 may be deposited within the recess and protected by depositing a coating of suitable material onto a surface of vane 23 over sensor 50 and connector 52. In other alternate embodiments a coating may be deposited onto a surface of vane 23, a trench may be formed within the coating and sensor 50 and connector 52 may be deposited within the trench. A protective coating may be deposited over sensor 50 and/or connector 52.

Connector 52 may extend from sensor 50 to a termination location, such as the peripheral edge of vane 23 so that a distal end 53 of connector 52 is exposed for connection to transmitter 54. Sensor 50 and connector 52 may be positioned on vane 23 to minimize any adverse affect on the aerodynamics of vane 23.

Figure 4:
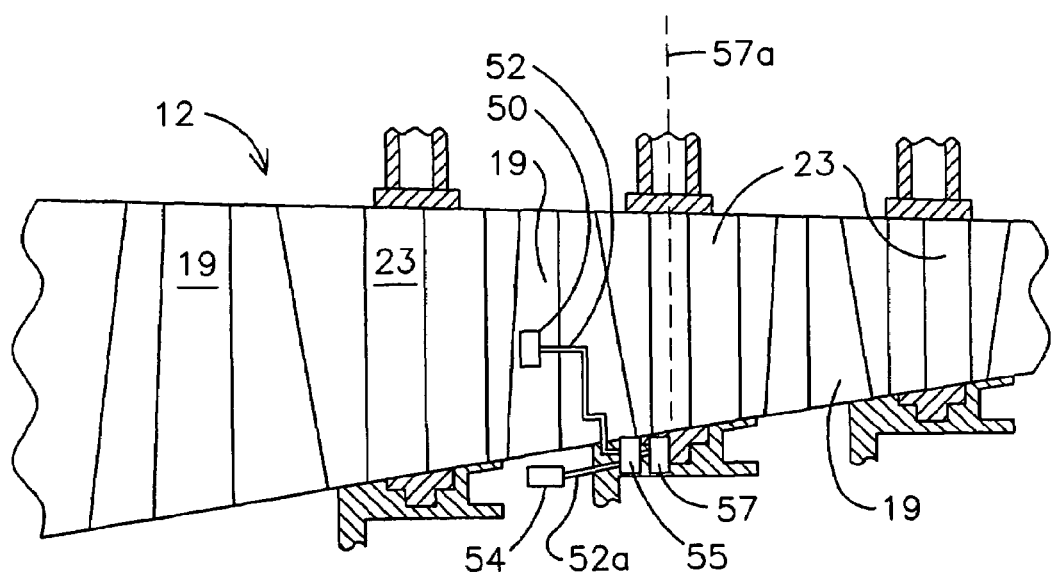
FIG. 4 is a schematic cross section of the compressor of FIG. 1.

In an embodiment, one or more sensors 50, such as strain gauges or thermocouples, for example, may be deposited on one or more turbine or compressor blades 18, 19. FIG. 4 illustrates an embodiment with respect to compressor 12. A connector 52 may be deposited to connect each sensor 50 to one or more transmitters 54 connected with blade 18,19. It will be appreciated that exemplary embodiments allow for a plurality of sensors 50 to be connected with a single transmitter 54 via respective connectors 52. For example, a sensor 50 may be deposited on each of a plurality of blades 18, 19. A connector 52 may be deposited to route a signal from each sensor 50 to a single transmitter 54.

Transmitter 54 and a rotating antenna 55 may be mounted proximate the root of blade 18, 19. Connector 52 may be routed from sensor 50 aft to the root of blade 18, 19 to connect sensor 50 with rotating antenna 55, which may in turn be connected with transmitter 54 via a connector 52a. A stationary antenna 57 may be installed on a turbine or compressor vane 22, 23 aft of the root of respective blade 18,19. A lead wire 57a may be routed from stationary antenna 57 out of compressor 12 or turbine 16 to broadcast a signal to system 30. In exemplary embodiments, such as that shown in FIG. 4, power may be generated through induction during operation of compressor 12 as will be appreciated by those skilled in the art. In this arrangement, transmitter 54 may transmit data to stationary antenna 57 via rotating antenna 55 and power may be supplied from stationary antenna 57 to transmitter 54.

It will be appreciated by those skilled in the art that one or more sensors 50 may be mounted to, such as by a spray deposition, each compressor blade 19 within a row of blades 19 mounted on a disk within compressor 12. A respective connector 52 may connect each sensor 50 to a respective transmitter 54 mounted proximate the root of each blade 19 within the row. Rotating antenna 55 may encircle the disk proximate the root of each blade 19 and be connected with each transmitter 54 via a respective connector 52a. One or more stationary antennas 57 may be installed on a compressor vane 23 aft of the row of compressor blades 19, or in another location, such as a compressor hub sufficiently proximate to rotating antenna 55 for signal broadcasting and receiving. Stationary antenna 57 may also encircle the row of blades 19. Rows of blades 18 in turbine 16 may be similarly configured.

Figure 5:
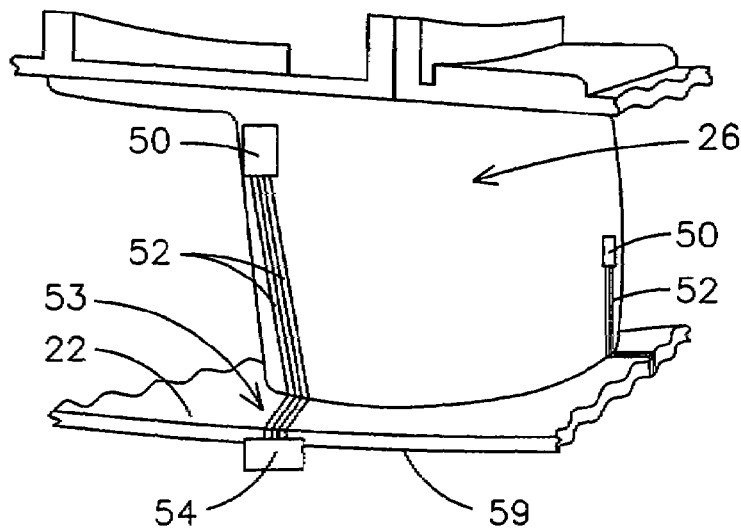
FIG. 5 is a perspective partial view of an exemplary embodiment of a smart component combustion in accordance with aspects of the invention.

FIG. 5 illustrates a partial view of a component, such as a vane 22 from turbine 16 having a barrier coating 26 deposited thereon. Sensor 50 and connector 52 may be embedded beneath an upper surface of barrier coating 26. Connector 52 may have a distal end 53 that is exposed at a termination location, such as proximate a peripheral edge 59 of vane 22 for connection with transmitter 54. In an embodiment transmitter 54 may be surface mounted to vane 22 or embedded within coating 26 proximate peripheral edge 59. Alternate embodiments allow for transmitter 54 to be located elsewhere such as on a platform (not shown) to which vane 22 is connected or in a cooling flow channel, for example, as will be recognized by those skilled in the art.

Figure 6A:
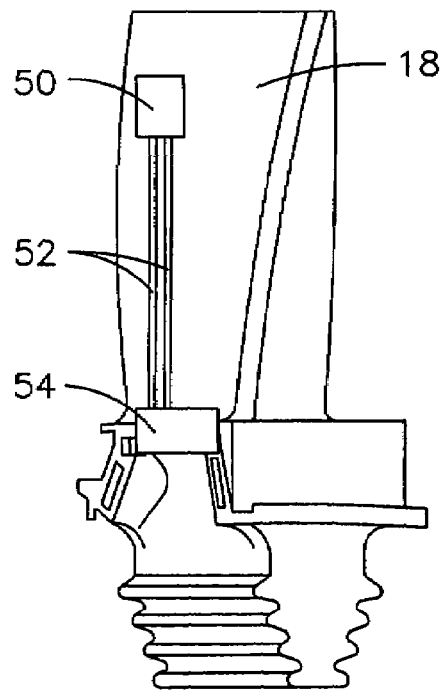
FIG. 6A is a schematic view of an exemplary embodiment of the component of FIG. 5.
Figure 6B:
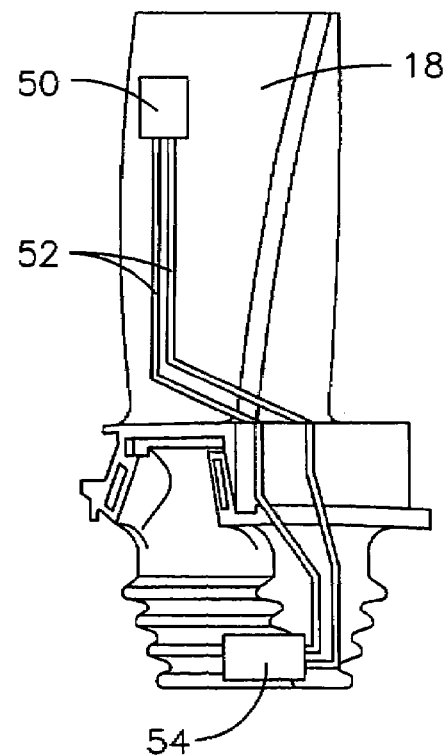
FIG. 6B is a schematic view of an exemplary embodiment of the component of FIG. 5.
Figure 6C:
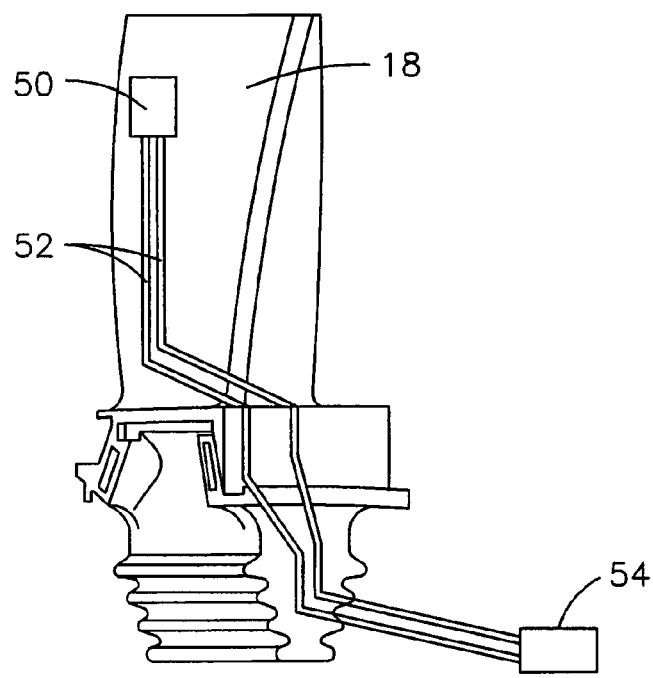
FIG. 6C is a schematic view of an exemplary embodiment of the component of FIG. 5.

FIG. 6A illustrates a schematic plan view of a blade 18 having an exemplary sensor 50 connected therewith and connector 52 connecting sensor 50 with transmitter 54. Transmitter 54 may be powered through induction generated within turbine 16 during operation that will be appreciated by those skilled in the art. FIGS. 6A, 6B and 6C illustrate exemplary embodiments of a turbine blade 18 having transmitter 54 placed in various locations. In FIGS. 6A and 6B transmitter 54 may be mounted to blade 18 and FIG. 5C illustrates that transmitter 54 may be located remote from blade 18. For example, transmitter 54 may be located remotely from blade 18 such as within a disk (not shown) to which a plurality of blades 18 is attached. In this respect, transmitter 54 may be maintained in a cooler location outside the hot gas path, which may increase the transmitter's useful life. Locating transmitter 54 remote from blade 18 allows for using an external power source for powering transmitter 54 rather than using a battery or induction.

A power supply may also be attached to sensor 50 to provide additional functionality to the sensor. This additional functionality could include mechanical actuation as a result of feedback to the sensor 50 output. Such an integrated system may be applicable for components, such as ring segments for real-time gap control.

The exemplary embodiments of compressor vane 23 and turbine blade 18 illustrated in FIGS. 3-6A, 6B and 6C configured with self-contained sensors 50 and connectors 52 are advantageous in that they may be prefabricated for installation in combustion turbine 10 by a field technician. Embodiments allow for a distal end 53 of connectors 52 to be exposed at a termination location. This location may be proximate a peripheral edge of a component or other location. This allows a field technician to quickly and easily connect connector 52 to a transmitter 54 regardless of its location.

Providing components of combustion turbine 10, such as vanes 23 and/or blades 18 with pre-installed sensors 50 and connectors 52 is a significant advantage over previous techniques for installing such components in the field, which typically required an extensive array of wires to be routed within combustion turbine 16. Providing components with pre-installed sensors 50 and connectors 52 allows for monitoring the condition of those specific components during operation of combustion turbine 10.

Embodiments of the invention allow for sensor 50 to be configured to perform a wide range of functions. For example, sensor 50 may be configured to detect wear of a single component or between two components, measure heat flux across a component's coating, detect spalling of a coating, measure strain across an area of a component or determine crack formation within a component or coating. U.S. Patent Application having application Ser. No. 11/018,816 discloses embodiments of a system that generally involves monitoring the wear of a component that may be configured in accordance with embodiments of the present invention.

Wear sensors 50 may be configured as embedded electrical circuits in a contact surface of a component, such as a tip of blade 18 and the circuit may be monitored by monitoring system 30 for indications of wear. By positioning a circuit at the wear limit, or at prescribed depths from the component's surface, the condition of the surface may be continuously monitored and system 30 may provide an operator with an advanced warning of service requirements.

It will be appreciated that sensor 50 may be configured for wear detection and prefabricated within a component for use within combustion turbine 10 either alone or in combination with a means for transmitting 52 in accordance with aspects of the present invention. In this respect, the signals extracted for detection of wear may be conducted via connectors 52 to transmitter 54, which may transmit the signals via wireless telemetry to a transceiver 56 and subsequently system 30.

Embodiments of the present invention allow for monitoring and control system 30 to collect and store historical data with respect to a component's wear and correlating the component's wear with the operating conditions of combustion turbine 10 responsible for producing the wear. This may be accomplished by continuously interrogating turbine 16 conditions, for example, by the deposition of piezoelectric devices and/or other sensors 50 configured for providing a continuous data stream indicative of the loading conditions and vibration frequency experienced by various components within turbine 16. This data may be correlated to data indicative of a component's wear and used for predictive maintenance or other corrective actions.

Figure 7:
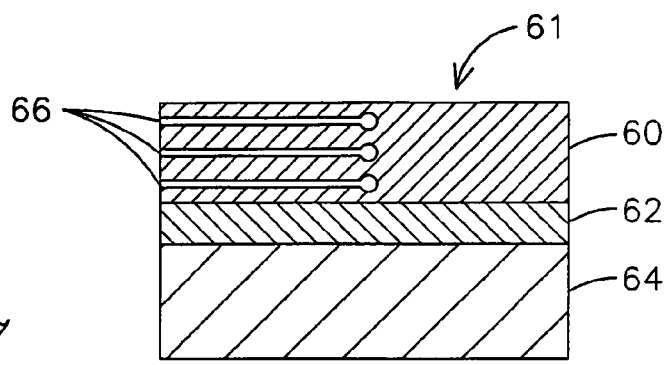
FIG. 7 is an exemplary embodiment of a heat flux sensor.

FIG. 7 illustrates another exemplary embodiment of a sensor 50 that may be configured as an exemplary heat flux sensor 61 for measuring heat flux across a barrier coating such as a thermal barrier coating (TBC) 60, which may be yttrium-stabilized zirconium. Using known techniques, thermal barrier coating 60 may be deposited on a bond coat 62, which may be deposited on a substrate 64. Substrate 64 may be various components such as a superalloy suitable for use in turbine 16, and in an embodiment may a blade 18. The heat flux may be used to obtain the surface temperature of substrate 64 without having to expose the surface of substrate 64 to the surface temperature experienced by the upper surface of thermal barrier coating 60.

Thermocouples 66 may comprise a material having a coefficient of thermal expansion that substantially matches that of the material within which they are deposited, such as thermal barrier coating 60. In an embodiment, a plurality of temperature sensors, such as K-type thermocouples 66 may be embedded within a thermal barrier coating 60 with thermocouples 66 located vertically over each other as shown in FIG. 6. In an embodiment, thermocouples 66 may include a NiCr/NiAl thermocouple junction. Alternate embodiments allow for thermocouples 66 to be fabricated of other materials such as Pt and Pt—Rh for high temperature applications such as those within turbine 16.

Heat flux sensor 61 may be formed in different geometries to achieve a desired signal-to-noise ratio. Each thermocouple 66 may be approximately 25 microns thick but this thickness may vary depending on the application. Because the thermal barrier coating 60 may be several times as thick as thermocouples 66 they will not significantly alter the profile or performance of thermal barrier coating 60. Embodiments allow for post deposition laser micromachining to achieve a desired junction density.

As heat flows vertically into or out of thermal barrier coating 60, each thermocouple 66 will record a different temperature measurement. By measuring the temperature differences and knowing the thickness and thermal conductivity of thermal barrier coating 60, the heat flux can be obtained. Thermocouples 66 may be connected with a means for transmitting 52 as described herein so that the respective temperature measurements taken by each thermocouple 66 may be wirelessly transmitted to monitoring and control system 30.

Figures 8, 9:
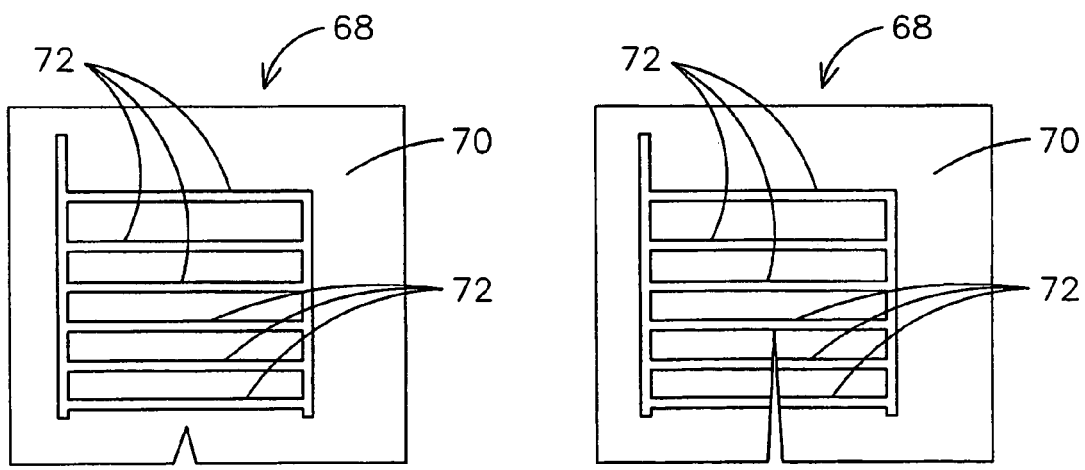
FIGS. 8 and 9 illustrate an exemplary embodiment of a strain gauge and a crack propagating to different lengths.

FIGS. 8 and 9 illustrate an exemplary embodiment of a sensor 50 that may be configured as an exemplary sensor 68 configured for detecting and/or measuring strain or a crack within a location of interest such as substrate 70. For example, substrate 70 may be a location of interest of a surface area of a blade 18, or it may be other locations of interest within or at the surface of thermal barrier coating 60 or bond coat 62. It will be appreciated that sensor 68 configured in this manner may be used in numerous places throughout combustion turbine 10. The sensors described in FIGS. 8 and 9 describe the utilization of the change in resistance to result in a strain output. Other embodiments of strain gauges could also include capacitive changes to determine the local strain values.

In this respect, critical engineering components, such as blades 18,19 and vanes 22, 23 are nearly universally subjected to some form of mechanical and/or thermo-mechanical cyclic loading. Aspects of the invention allow for the assessment of component service life by the intermittent or continuous, in-situ measurement of applied strains and crack detection with respect to that component. This may be accomplished by the placement of embedded strain gages and crack sensors 68 in various locations within combustion turbine 10. Sensors 50 configured as a strain gauge 68 may be formed using a NiCr material for use in lower temperature applications, such as in compressor 12 of combustion turbine 10.

Sensors 68 may be used as crack sensors by placing them at locations or points where cracks are known or likely to appear. A crack sensor gauge 68 may be optimized for size, crack propagation, and crack extent through appropriate choice of gauge 68 parameters. Such parameters may include the footprint of gauge 68, spacing of fingers 72, and orientation of fingers 72 with respect to the direction of a predicted crack propagation. Crack formation in substrate 70 gives rise to a large, abrupt change in the strain gauge response, and may be detected by continuously monitoring the sensor 68 output for abrupt signal changes using known signal processing techniques. Data indicative of the signal change may be conducted via a means for transmitting 54 to a transceiver 56 and subsequently transmitted to monitoring and control system 30 via wireless telemetry.

In an exemplary embodiment, a strain gauge sensor 68 may be bonded to or deposited on a surface of a compressor blade 19 and positioned so that bending stress on blade 19 varies the output signal from sensor 68. Connector 52, which may be wire leads, are routed to a transmitter 54 located on a rotating collar internal to compressor 12. Transmitter 54 may have an onboard bridge completion and provide a regulated voltage to sensor 68. As the output signal from sensor 68 varies an RF signal from transmitter 54 varies proportionally. The RF signal may be transmitted to a transceiver 56, which receives the RF signal and converts it into a voltage signal proportional to the strain detected by sensor 68. The RF signal may be transmitted to system 30. An exemplary transmitter 54 may pick up changes in strain from about 30 Hz to about 30 KHz.

Embodiments of the invention allow for using crack sensors 68 to monitor crack growth during operation of combustion turbine 10 and verify design models by varying component operating parameters until cracks are detected with the crack sensors 68. The design models will be calculated for the same operating parameters to see if they successfully predict crack growth and formation, and will be modified accordingly.

Monitoring and control system 30 may collect and store data indicative of strain and crack measurements from numerous components in critical locations within combustion turbine 10, such as blades 18, for example. Such data may be analyzed over time to develop a strain history for each component. A component's strain history may include the magnitude and orientation of strains, and the occurrence of overloads under cyclic loading. An appraisal of fatigue damage may be developed and used for predictive maintenance.

Embodiments of the present invention allow for deploying a plurality of sensors 50 throughout combustion turbine 10 by either surface mounting them to components or embedding them within respective component barrier coatings to collect specific component condition data and transmit that data using wireless telemetry to monitoring and control system 30. This approach is advantageous in that it allows for the replacement, repair and maintenance decision-making processes to be based on the condition of specific components during operation of combustion turbine 10.

In this respect, specific component condition data may be received by antenna 32 and receiver 33 then stored in database 36 by CPU 34. Embodiments allow for specific component condition data to be collected and presented to an operator in real time via display 38. This allows for an operator to make instantaneous decisions regarding the operation of combustion turbine 10 in response to the condition of a specific component or components.

Historical data may be compiled and analyzed with respect to each component for making repair, replacement or maintenance decisions with respect to that component. Operating conditions and specific components of combustion turbine 12 may be monitored sets of conditions may be isolated that are indicative of a component or components needing to be repaired or replaced, or of corrective action to be taken with respect to operation of the gas turbine. These aspects allow for significant improvement in predictive maintenance schedules.

Figure 10:
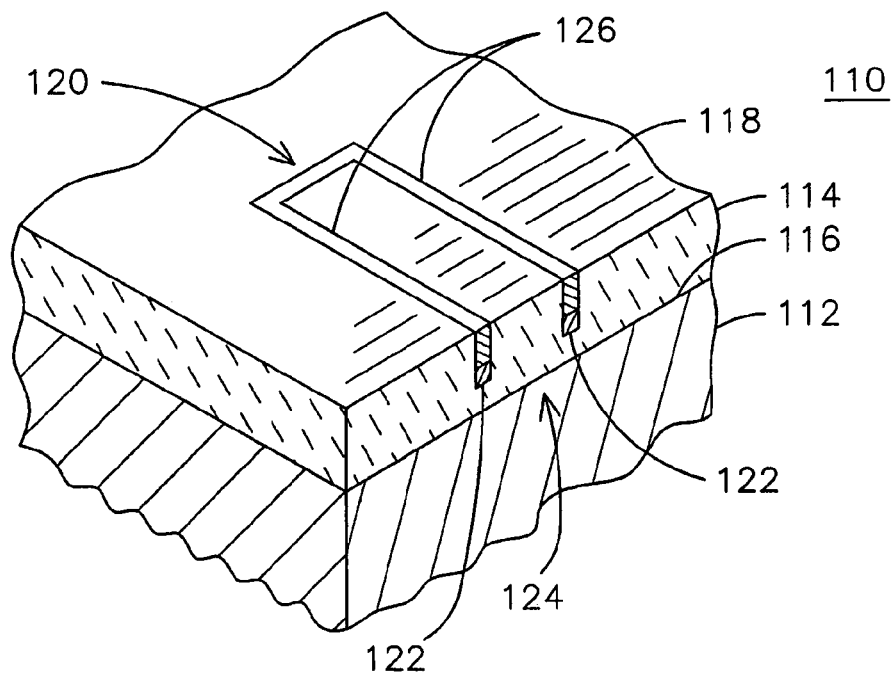
FIG. 10 is a partial perspective view of a component having a sensor embedded within a layer of thermal barrier coating material disposed over a substrate material.

FIG. 10 is a partial perspective illustration of a component 110 formed of a substrate material 112 having a barrier coating such as a layer of thermal barrier coating 114 disposed on one surface 116. The component 110 may be part of a gas turbine engine 10 of FIG. 1, for example, or any other machine wherein a base material must be protected from an external environment by a layer of a barrier material. In an embodiment, component 110 may be an airfoil member, such as a turbine blade 18 disposed in the hot gas flow path of a engine 10 with an oxide or non-oxide ceramic TBC 14 such as mullite, silicon carbide or a zirconium-based ceramic overlying a superalloy substrate material 112.

Component 110 may alternatively be fabricated from a ceramic matrix composite (CMC) substrate coated with an environmental barrier coating (EBC) or a thermal barrier coating (TBC). Because the integrity of the coating 114 is critical to the overall integrity of the component 110, it is useful to obtain operating parameter information that directly affects the performance of the coating 114. Such information is obtained by embedding a sensor, such as a sensor 50 below the exposed surface 118 of the TBC 114. The sensor is not visible in FIG. 10 but may be located below surface 118 in the sensing location indicated generally by numeral 120.

The sensor may be one that provides a signal indicative of temperature, strain, crack initiation, chemical changes, vibration, pressure or other parameters of interest. These sensors themselves could be multi-layered containing a combination of electrodes and the functional body. Conductors 122 may also be located below surface 118 may route the signal produced by the sensor away from sensing location 120 to a termination location, which may be a connection location indicated generally by numeral 224 where they can conveniently exit the component 110. Conductors 122 may function similarly to connectors 52 for routing a signal from a sensor, such as a sensor 50 to a transmitter 54 for transmission to system 30 via wireless telemetry. The sensor and the conductors 122 may be insulated from the surrounding environment by a layer of insulating material 126.

Figure 11:
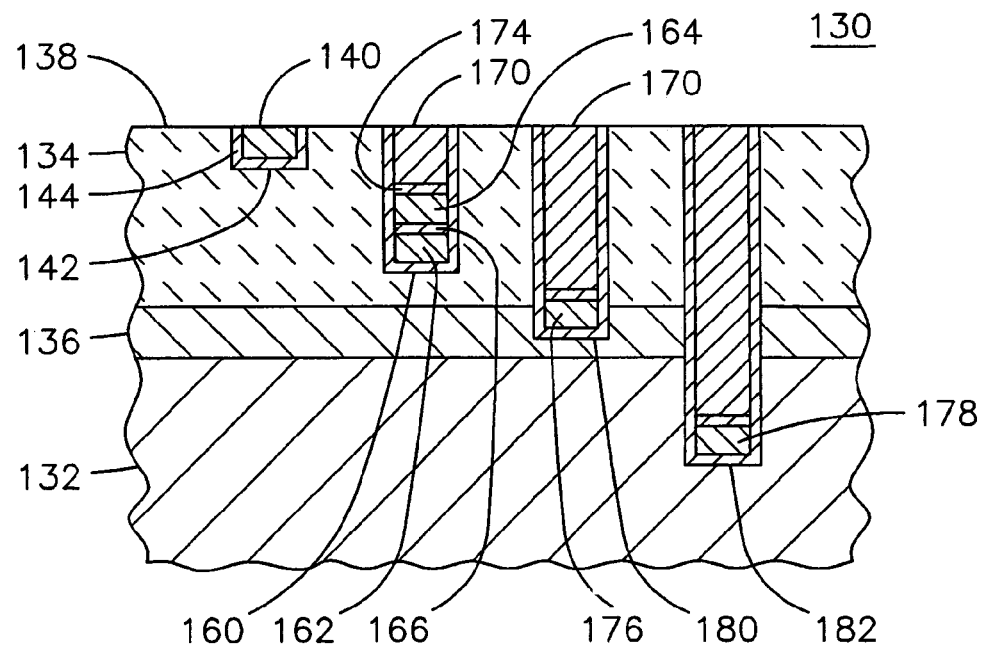
FIG. 11 is a partial cross-sectional view of a component having a plurality of sensors embedded at varying depths below a surface of the component.

FIG. 11 is a partial cross-sectional view of another component 130 having a substrate material 132 covered by a barrier coating such as a layer of a thermal barrier coating material 134 for use in a very high temperature environment. As is well known in the art of TBC coatings, a bond coat 136 such as an MCrAlY material may be deposited on the substrate 132 prior to the application of the TBC material 134 to improve the adherence of the coating 134 to the substrate 132.

Component 130 may be instrumented by a plurality of sensors, such as sensors 50 embedded at a plurality of depths below a surface 138 of the TBC material 134 that is exposed to the external environment. A first sensor 140 is deposited in a relatively shallow trench 142. Trench 142 may be lined with an electrically insulating coating 144 such as aluminum oxide to prevent the grounding of sensor 140 to the TBC material 134. Sensor 140 may take any form known in the art, for example a thermocouple formed by a bimetallic thermocouple junction or other sensors described herein. The surface location of sensor 140 suggests that it may be useful for sensing a parameter related to the external environment, such as temperature or a chemical parameter.

Figure 12:
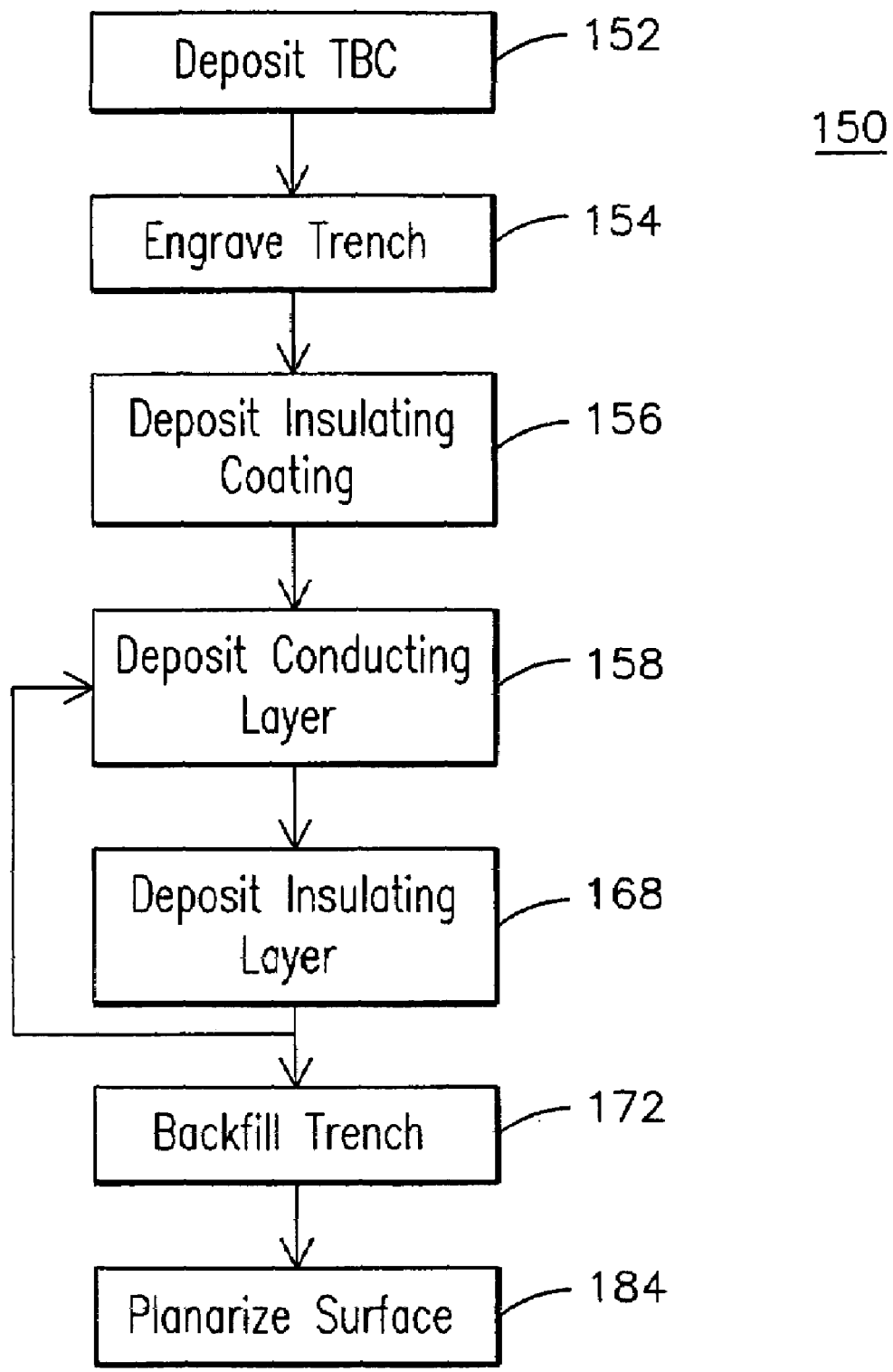
FIG. 12 is a process diagram illustrating steps in a method of manufacturing the component of FIG. 11.

FIG. 12 illustrates the steps of a process 150 that may be used during the manufacturing of the component 130 of FIG. 11. In step 152, a layer of thermal barrier coating material 134 may be deposited onto a substrate 132. After step 152, the component is completed in its normal operating shape as it may be used without embedded instrumentation. One skilled in the art may appreciate, therefore, that the process 150 may be applied to newly fabricated components or it may be back fit to an existing component that is in inventory or that has been in service.

In step 154, a trench 142 may be formed in a surface 138 of the component 130. Trench 142 may be formed to any desired shape by any known method, such as by laser engraving trench 142 to have a generally rectangular cross-section with a predetermined width and depth. Variables for such a laser engraving process include spot size, power level, energy density, pulse frequency, and scan speed. These variables together affect the trench width, depth, material removal rate and the cost of manufacturing. Trench 142 may have a constant cross-sectional size and shape along its entire length, or it may vary in size and/or shape from one region to another. For example, in the component 110 of FIG. 10, a trench formed in the sensing location 120 may have different dimensions than the trench extending from the sensing location 120 to the connecting location 124, since the sensor and the conductors 122 may have different geometries. The trench 142 may also be inclined to the surface, i.e. varying in depth along its length, which in some applications may provide improved mechanical integrity within the component.

After trench 142 is formed at step 154, an insulating coating 144 may be applied to the surfaces of the trench 142 at step 56 in order to provide electrical isolation between sensor 140 and TBC material 134. Insulating coating 144 may be deposited by any known method such as chemical vapor deposition (CVD) to a thickness sufficient to achieve a desired level of electrical isolation. Once the trench 142 is formed at step 154 and insulated at step 156, the sensor 140 may be formed by depositing the appropriate material or materials into trench 142 at step 158. Any known material deposition process providing the desired material properties may be used. Such processes are common in the fields of rapid prototyping, thin and thick film deposition, and thermal spraying, and include, for example, chemical vapor deposition, plasma spray, microplasma spray, cold spray, electroplating, electrophoretic deposition, HVOF, sputtering, CCVD, sol-gel and selective laser melting. Processes typically used for the fabrication of multi-layer thick film capacitors may also be used, such as the application of pastes and tapes of the desired materials.

After the deposition of material, a heat input may be used to sinter the material, thereby increasing the mechanical integrity of the sensor. This can be done either by heating using a flame, plasma, furnace annealing or localized laser energy application. In the selective laser melting (SLM) process, powdered material having a predetermined chemistry may be deposited into the trench and melted with the energy of a laser beam to form the respective portion of the sensor 140 of FIG. 11 or the interconnecting conductors 122 of FIG. 10. For example, to form a thermocouple, platinum powder may be deposited into one portion of trench 142 and solidified by a SLM process. Platinum-rhodium powder may then be deposited into a second portion of trench 142, either along the trench length or as a second vertical layer, and solidified by a SLM process to contact the platinum material to form the thermocouple junction.

Note that the geometry of trench 142 may have a direct effect on the geometry of the sensor 140. Accordingly, it is possible to affect the operating parameters of sensor 140 or interconnecting conductors 122 by controlling the dimensions of the respective trench 142. For example, the resistance of a conducting line formed within a trench will be affected by the width of the trench. The laser engraving process of step 154 may be closely controlled to achieve a desired trench geometry. Certain commercially available processes for depositing a conductor onto a flat surface by thermal spraying may not produce the fine features that may be necessary for sensors and conductive lines. Such processes may rely on a subsequent material ablation process to achieve a desired geometry. Because trench 142 provides control of the width of the feature, no such trimming step is needed in the process 150 of FIG. 12.

FIG. 11 also illustrates a second trench 160 formed in the TBC material 134 to a second depth that is farther below surface 138 than trench 142. By forming a plurality of trenches 142,160 at a plurality of depths below surface 138, it is possible to place sensors, such as sensors 50 at more than one depth within the component 130, thereby further augmenting the available operating parameter data. In the embodiment of FIG. 11, trench 160 contains two vertically stacked conducting layers 162,164 separated by an insulating layer 166. The conducting layers 162,164 may form two portions of a sensor, or two conducting lines for connecting a sensor to a connecting location. 1As illustrated in FIG. 12, the two conducting layers 162, 164 may be formed by first depositing conducting layer 162 at step 158, and then depositing an insulating layer 166 at step 168 using any desired deposition technique, such as CVD.

Steps 158,168 are then repeated to deposit conducting layer 164 and insulating layer 174. The width of these layers is controlled by the width of trench 160 and the thickness of these layers may be controlled as they are deposited to achieve predetermined performance characteristics. For example, the thickness of insulating material 166 will affect the impedance between the two conducting layers 162,164. Conducting layer 164 is then isolated from the external environment by backfilling the trench 160 with a barrier material such as thermally insulating material 170 at step 172. Insulating material 170 may be the same material as TBC material 134 or a different material having desired characteristics. Insulating material 170 may be deposited by any known deposition technique, including CVD, thermal spraying, selective laser melting, or selective laser sintering. Selective laser melting and selective laser sintering processes are known in the art, as exemplified by Chapters 6 and 7 of "Laser-induced Materials and Processes For Rapid Prototyping" by L. Lu, J. Y. H. Fuh, and Y. S. Wong, published by Kluwer Academic Publishers.

Additional sensors 176,178 may be disposed at preselected depths within component 130 by forming respective trenches 180, 182 to appropriate depths. Trenches 180, 182 may be backfilled with insulating material 170 to the level of surface 138 at step 172. Planarization of surface 138 may be performed at step 184, if necessary, such as when surface 138 forms part of an airfoil. By forming a trench to a desired depth, a sensor may be embedded to within the TBC material layer 134, to within the bond coat material layer 136, to within the substrate material 132, or to a depth of an interface between any two of these layers.

Thus, it is possible to develop actual operating parameter data across a depth of a component or across the depth of the thermal barrier coating. Such data may be useful for confirming design assumptions and for updating computerized models, and it may also be useful as an indicator of damage or degradation of a TBC coating. For example, a sensor 178 embedded below the TBC material 134 may produce a signal indicating a significant temperature rise in the event of cracking or spalling of the layer of TBC material 134. Alternatively, the detection of a predetermined level of vanadium, sodium or sulfur deposits by an embedded sensor 176 may announce conditions that would give rise to spalling and failure of the TBC coating 134 if the component were to remain in service for an extended period. This process facilitates the placement of sensors at any location on a fully assembled and coated part. Electrochemical sensors on the component surface can play an important role in determining the nature and effect of corrosion products present in the surrounding environment.

Figure 13:
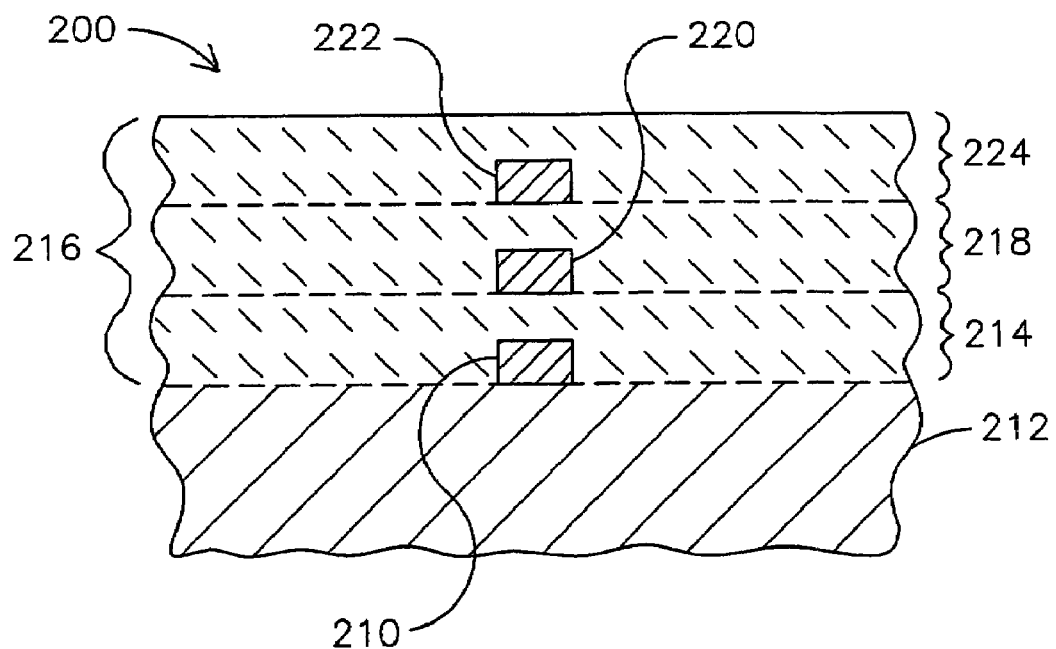
FIG. 13 is a partial cross-sectional view of a component having a plurality of sensors embedded at varying depths below a surface of the component.

FIG. 13 illustrates a component 200 that may be formed by depositing a first sensor 210 onto a surface of a substrate 212. Subsequently, a first layer 214 of a barrier coating 216, such as a CMC abradable coating system disclosed in U.S. Pat. No. 6,197,424, for example, is deposited over the sensor 210. A second sensor 220 is then deposited over the first layer 214. A second layer 218 of barrier coating 216 is then deposited, followed by the deposition of a third sensor 222 and third layer 224 of the barrier coating. In this manner, one or more sensors 210, 220, 222 may be embedded at a plurality of depths within the confines of a wall of a component 200. One may appreciate that the same component 200 may be formed without first sensor 210 by depositing the sensor 220 onto a surface of the component after it has received a first layer 214 of barrier coating material.

Embodiments of the structure of FIG. 13 may be useful for monitoring the amount of wear of an abradable coating system, since each of the sensors 210, 220, 222 may become exposed at a different time as the coating 216 undergoes wear due to abrasion. Signals generated by the respective sensors 210, 220, 222 are responsive to the wear of coating 216 and may be used in an improved clearance control program for predicting the remaining useful life of an abradable coating and/or for estimating the amount of leakage past an abradable seal.

Figure 14:
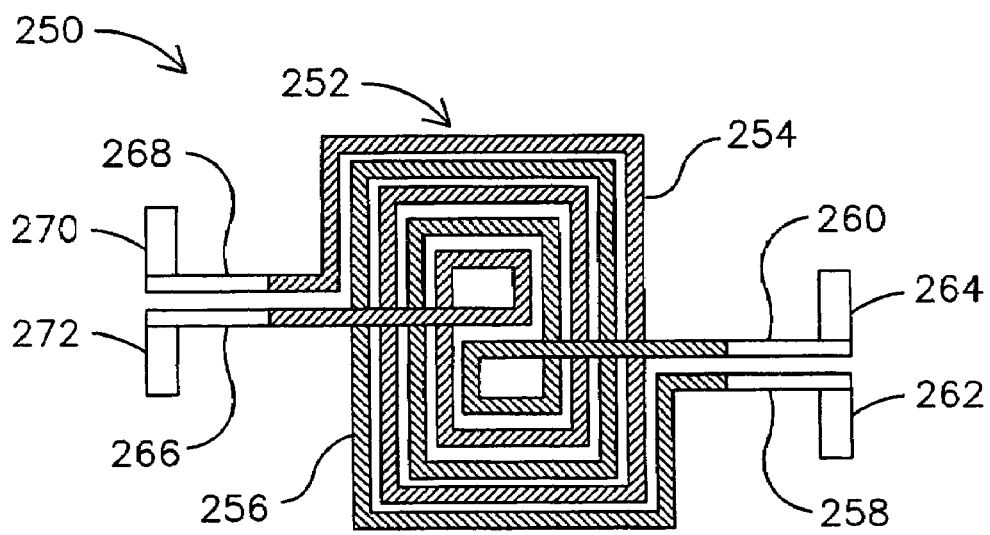
FIG. 14 is schematic plan view of an exemplary planar proximity sensor.

For example, FIG. 14 illustrates a schematic plan view of an exemplary planar proximity sensor 250 that may be formed with circuitry 252 deposited directly onto a substrate or at varying depths within a coating such as an abradable coating system 216. Thermal sprayed abradable coating systems 216 are typically applied for gas path clearance control, which influences power output and efficiency of combustion turbine 10. Coating systems 216 are usually porous coatings that abrade when contacted by a moving structural component, such as the tips of blades 18 and are designed not to damage the contacting surface. Information with respect to the wear behavior of coating system 216 may be used to predict the useful life of the coating, prevent catastrophic interaction between components and allow for improved control of combustion turbine 10.

Exemplary embodiments of circuitry 252 may include a first planar winding or coil 254 and a second planar winding or coil 256. First coil 254 may be used to charge the element with an AC signal and second coil 256 may be used to measure the response within the surrounding material such as abradable coating system 216. Coils 254, 256 may be made of nonmagnetic conductor material such as Ni—Cr alloy, copper, silver or other suitable materials. A dielectric insulator such as alumina, spinel or other suitable material may be used as needed to insulate the coils from surrounding conductive material such as substrate 212 or certain abradable coating systems 216 that include conductive material. A dielectric insulator may not be needed for applications within certain other abradable coating systems 216 such as a zirconium-dioxide based CMC system, for example.

First planar coil 256 may be conductively connected by leads 258, 260 to respective conductors 262, 264. Conductors 262, 264 may be in electrical communication with a power source for applying a voltage to sensor 250. Similarly, second planar coil 254 may be conductively connected by leads 266, 268 to respective conductors 270, 272. In alternate embodiments a single coil may be used for both the interrogation and measurement of the response signal, typically at lower frequencies than two coils, as a function of performance requirements of sensor 250.

One or more conductive connectors, such as a connector 52 may be provided as a means for routing data signals indicative of the measured response from sensor 250 to a transmitter 54, which may be configured for wirelessly transmitting the data signal to a transceiver 56, such as those shown in FIG. 1. Connector 52 may be one or a plurality of electrical leads for conducting a signal from sensor 250 via conductors 270, 272 to a transmitter such as surface mounted transmitter 54. Alternate embodiments allow for the signal to be conducted to an antenna (not shown), which may be an inductively couple spiral coil for wirelessly transmitting data signals from sensor 250 to a transmitter 54 and/or transceiver 56.

An exemplary embodiment of sensor 250 may be configured to produce an eddy current circuit to detect intrusions into abradable coating system 216. Such intrusions may be the tips of rotating blades 19 in compressor 12 or blades 18 in turbine 16 abrading coating 216 during operation of combustion turbine 10. Intrusions between other components may be detected within the casing of compressor 12 or turbine 16 at various other places of interest.

By way of example, a sensor 250 having circuitry 252 deposited within abradable coating system 216 will produce an eddy current that is interfered with upon intrusion into system 216 by a metallic blade tip. The phase between first and second coils 254, 256 may be used to measure absolute distances, which may be correlated to the wear behavior of abradable coating system 216. Embodiments of sensor 250 including circuitry 252, leads 258, 260, 266, 268 and conductors 262, 264, 270, 272 may be deposited using thermal spray deposition, for example, such as the conformal direct write technology disclosed in U.S. Pat. No. 6,576,861. Other deposition processes may be used as recognized by those skilled in the art.

Embodiments of sensor 250 may be an inductive proximity sensor having circuitry 252 that generates an electromagnetic field and detects any changes in a resonant circuit caused by eddy current losses induced in a conductive material influencing the magnetic field. When an AC voltage is applied to sensor 250 an oscillating current flows through the first coil 254 and radiates an electromagnetic field from coil 254 to the passive coil 256 of sensor 250. When an electrical conductor or metal component such as a tip of blade 18, for example, enters the electromagnetic field, eddy currents are drawn from the oscillator and induced into the blade tip. The losses in energy caused by the eddy currents may be correlated to the distance and position of the blade tip relative to sensor 250.

Figure 15:
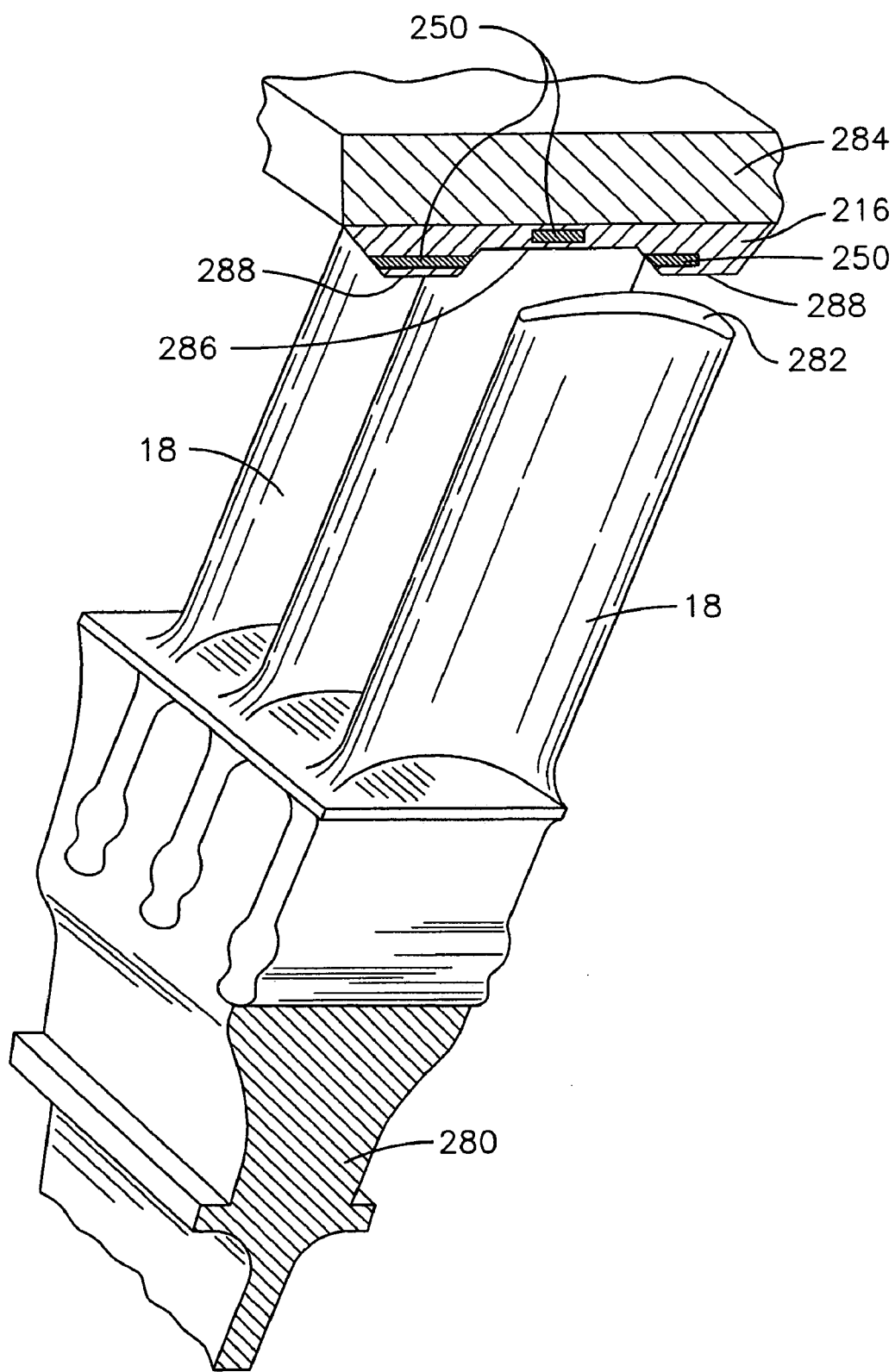
FIG. 15 is a perspective view of planar proximity sensors embedded in an abradable coating system for measuring blade tip clearance.

FIG. 15 is a partial perspective view of turbine blades 18 intruding into abradable coating system 216 during rotation of the blades such as when combustion turbine 10 is in operation. A plurality of blades 18 is mounted to a rotor disk 280. Blade tip 282 is located just inside an inner wall 284, which may be a blade outer air seal or ring segment of combustion turbine 10 as recognized by those skilled in the art. Abradable coating system 216 may be deposited on a ring segment 284 so that a groove 286 is abraded within the coating as blades 18 rotate. One or more sensors 250 may be deposited on or within the inner surface of ring segment 284, or within abradable coating system 216. Ring segment 284 may include a row of ring segment sections that circumscribe the row of blades. Embodiments of sensor 250 may be deposited at predetermined depths within abradable coating system 216 selected based on a desired sensitivity of the sensor for detecting intrusion of a blade tip 282 into the abradable coating system. It may be desirable to deposit sensor 250 away from the inner surface of ring segment 284 to minimize the influence of ring segment 284 on sensor 250 and increase the sensitivity of sensor 250 to the passing of blade tip 282.

Sensors 250 are depicted schematically as boxes in FIG. 15 but it will be appreciated they may deposited in various configurations, orientations and locations. For example, circuit designs could be optimized to obtain desired signal to noise ratios depending on the location of the deposited circuit. In an embodiment, a magnetic coating 285 may be applied to blade tips 282 for applications below the Curie point of the magnetic coating, such as an early stage compressor 12 component. In this aspect, a single coil, such as one of coils 254, 256 may be deposited within a coating, or on or beneath a surface of a component such that the passing of blade tips drives a current. In such an embodiment, an active interrogation by an AC signal would not be required.

Embodiments of the invention may be used for continuously measuring the distance between blade tip 282 and one or more sensors 250 deposited on ring segment 284 or within abradable coating system 216 during operation of combustion turbine 16. In this aspect, a first distance between the end of a blade tip 282, or other selected locations on a blade 18, and the location of circuitry 252 of sensor 250 is known. The first distance may be calculated and stored in database 36 of monitoring system 30 and may be the distance between a blade tip 282 and circuitry 252 prior to the commissioning of a combustion turbine 10. The first distance may be other distances depending on the desired measurements to be taken. It will be appreciated that blade tip 282 may be coated with a barrier coating such as TBC 26 (FIG. 1). The composition and thickness of such a coating may be taken into account when selecting a configuration of circuitry 252 and calculating wear of coating system 216.

Abradable coating system 216 has a first or original thickness when initially deposited on ring segment 284, or after repairing the coating, and prior to being abraded by blade tips 282. One or a plurality of sensors 250 may be deposited within coating system 216 at varying selected depths from the original surface 288 of coating system 216. For instance, a plurality of sensors 250 may be deposited in spaced relation around the circumference of ring segment 284 for taking a respective plurality of measurements with respect to a row of blades 18.

As blade tips 282 of the row of blades 18 abrade coating system 216, groove 286 is formed within coating 216 that is approximately the width of blades 18. Blades 18 abrading coating 216 forms a second or operating thickness of that portion of coating system 216 that is not worn away by blade tips 282. This operating thickness may be defined as the thickness of coating system 216 from the surface of groove 286 to the interface 283 of coating system 216 with ring segment 284. The operating thickness may vary around the circumference of a respective ring segment 284 as appreciated by those skilled in the art.

The plurality of sensors 250 may continuously transmit data to monitoring system 30 indicative of the distance between a respective sensor 250 and a respective blade tip 282. Data indicative of the distances blade tips 288 have traveled into coating 216 may be stored in database 36. This data may be used by processor 34 to calculate the amount or depth of wear abradable coating system 216 is experiencing around the circumference of ring segment 284. In this respect, processor 34 may calculate the distance one or more blade tips 282 have traveled into coating system 216 during operation of combustion turbine 10 such as when going from start-up to full load.

Processor 34 may also calculate the size of gaps formed between a blade tip 282 and the inner surface of groove 286, including its edges, such as gaps formed when a blade tip 282 contracts from its maximum incursion into coating system 216. Such gaps may be calculated knowing the original thickness of coating 216, the maximum incursion of blade tips 288 into coating 216 and the current distance between sensors 250 and blade tips 288. This allows for estimating secondary gas path flow past through the gaps, which may be used for more efficient operation of combustion turbine 10 and improved predictive maintenance. Calculations made by processor 34 based on data from sensors 250 may be related to operating cycles of combustion turbine 10 for various purposes including improved control during cooling and service cycles, and avoidance of catastrophic failure.

Components within compressor 12 and turbine 16 may have different rates of thermal expansion so they expand and contract at different rates during heating and cooling of turbine 16. Blades 18 may expand more quickly than a rotor to which rotor disk 280 is mounted due to differences in their shape and mass. A control module of system 30 may use real-time and historical data from sensors 250 during a heating and/or cooling cycle of turbine 16 to prevent blade tips 282 from impinging on the inner surface of ring segment 284 by controlling various operating parameters of combustion turbine 10. For example, the turbine engine ramp rates and shut down schedule as well as scheduled spin cool cycles may be controlled in response to data received from sensors 250.

This data may also be used to control combustion turbine 10 to avoid other "pinch points", which may occur between numerous components within compressor 12 or turbine 16 during heating and/or cooling cycles. Such "pinch points" may develop for numerous reasons such as distortion of ring segment 284 due to servicing, uneven wear around ring segment 284, or the encroachment of ring segment 284 toward blade tips 282. This may happen due to vibration-induced wear on the hook portions of the ring segment holding it in place.

Figure 16:
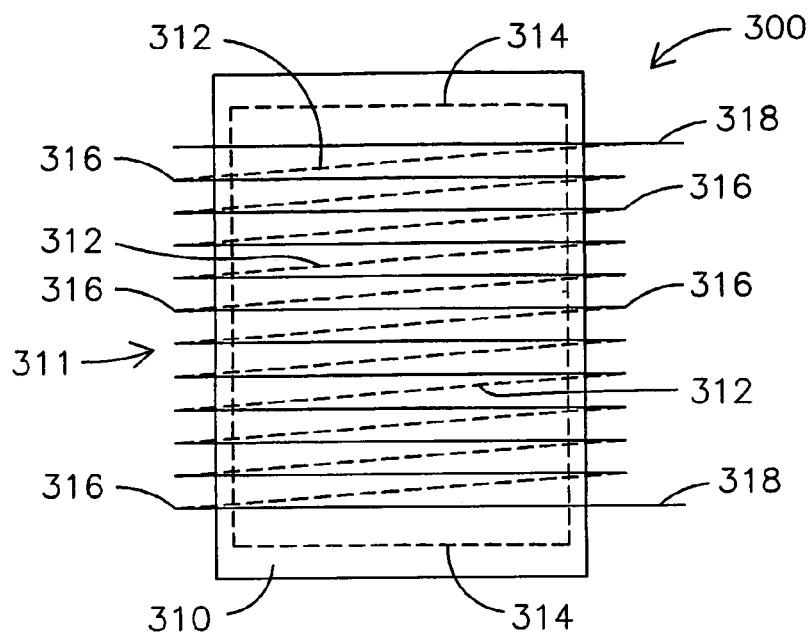
FIG. 16 is a plan schematic view of an exemplary proximity sensor having a magnetic core and winding.

Exemplary embodiments of the invention may include sensors having a winding around a magnetic core, which may provide a better signal response for certain applications and allows for selecting the orientation of the flux axis of the sensor. FIG. 16 illustrates an exemplary proximity sensor 300 comprising an insulating layer 310 that may be deposited directly onto a substrate such as ring segment 284. A first layer of nonmagnetic conducting material 312 may be deposited on insulating layer 310 to form a bottom half of a winding 311 that encapsulates a magnetic core 314. The first layer may be deposited as a plurality of spaced apart rows of material 312.

Magnetic core 314 may be a permalloy or ferrite material, and may be deposited on insulating layer 310 and conducting material 312. A second layer of nonmagnetic conducting material 312 may be deposited on magnetic core 314 to form a top half of winding 311. Joining the respective ends 316 of the first layer and the second layer of conducting material 312 may form winding 311. Conductive leads 318 may extend to a pair of respective conductors (not shown) for extracting a signal from sensor 300. It will be appreciated that sensor 300 may be deposited at various depths within a coating such as abradable coating system 216. Embodiments of sensor 300 may be configured to have an in-plane flux axis.

Figure 17:
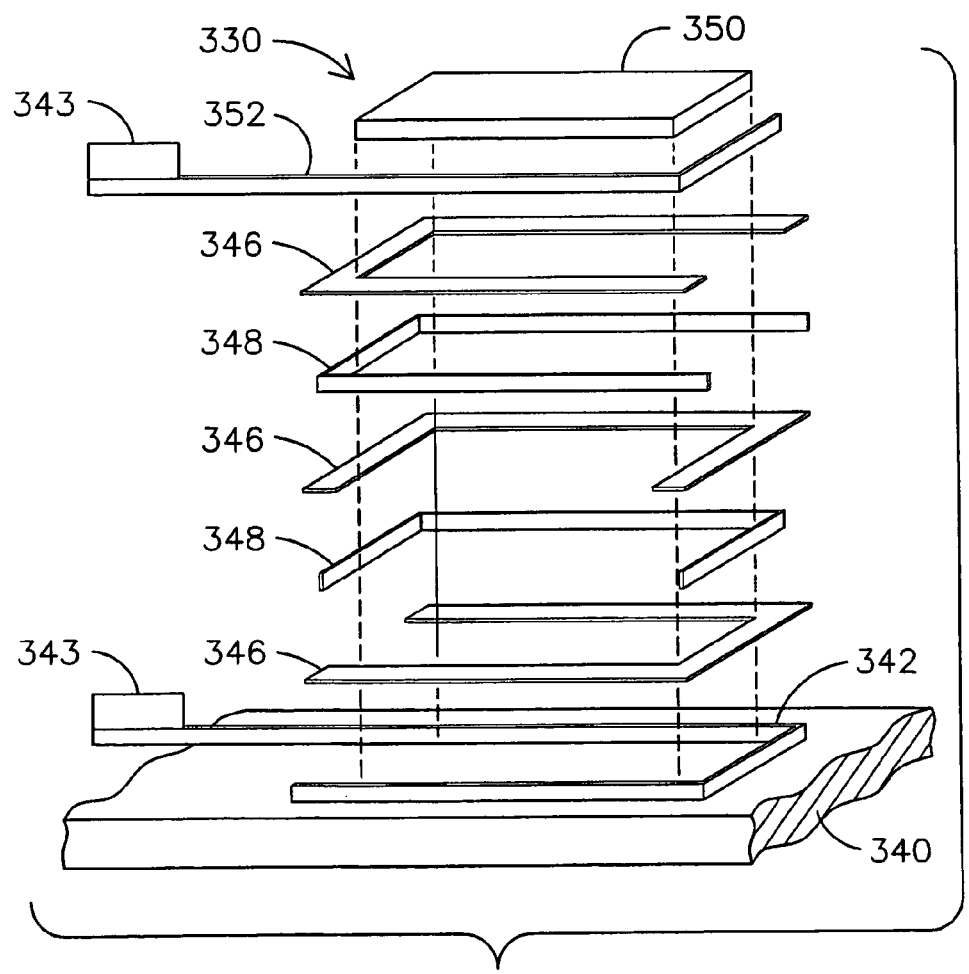
FIG. 17 is an exploded view of an exemplary proximity sensor having a magnetic core and winding.

FIG. 17 is an exploded view of an exemplary sensor 330 comprising an insulating layer 340 that may be deposited directly onto a substrate such as ring segment 284. A first layer of nonmagnetic conducting material 342 may be deposited on insulating layer 340 with a portion extending to a conductor pad 343. Alternating layers of insulating material 346 and conductive material 348 may be deposited to form a spiral or winding around a magnetic core 350, which may be deposited on insulating layer 340. A top layer of conducting material 352 may be deposited and extend to a conductive pad 343. It will be appreciated that sensor 330 may be deposited at various depths within a coating such as abradable coating system 216. Embodiments of sensor 330 may be configured to have an out of plane flux axis.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

We claim as our invention:

1. A component for use in a combustion turbine, the component comprising:
    a substrate;
    an abradable coating system deposited on the substrate;
    a planar proximity sensor deposited beneath a surface of the abradable coating system and comprising circuitry configured to detect intrusion of an object into the abradable coating system; and
    at least one connector in electrical communication with the planar proximity sensor for routing a data signal from the planar proximity sensor to a termination location.

2. The component of claim 1 further comprising:
a transmitter in electrical communication with the at least one connector for wirelessly transmitting the data signal outside the combustion turbine.

3. The component of claim 1 further comprising a trench formed in the abradable coating system wherein the planar proximity sensor is deposited within the trench.

4. The component of claim 1 further comprising:
a plurality of trenches formed at respective different depths below the surface of the abradable coating system; and
a planar proximity sensor deposited within each of the plurality of trenches.

5. The component of claim 1, the component comprising a ring segment of the combustion turbine, the planar proximity sensor deposited at a predetermined depth beneath the surface of the abradable coating system, the predetermined depth selected based on a desired sensitivity of the planar proximity sensor for detecting intrusion of a blade tip of a combustion turbine into the abradable coating system.

6. The component of claim 1, the planar proximity sensor comprising at least one planar winding selected to generate an electromagnetic field in response to an applied voltage and detect changes in a resonant circuit caused by eddy current losses induced in the object when influencing the electromagnetic field.

7. The component of claim 6, the planar proximity sensor comprising a first planar winding and a second planar winding.

8. The component of claim 1, the planar proximity sensor comprising a magnetic core and a winding around the magnetic core.

9. The component of claim 8, the winding comprising a first layer of nonmagnetic conducting material above the magnetic core and a second layer of nonmagnetic conducting material beneath the magnetic core.

10. The component of claim 8, the winding comprising alternating layers of a nonmagnetic conducting material and an insulting material.

* * * * *

UNITED STATES PATENT AND TRADEMARK OFFICE
CERTIFICATE OF CORRECTION

PATENT NO.       : 7,618,712 B2
APPLICATION NO.  : 11/269044
DATED            : November 17, 2009
INVENTOR(S)      : Sabol et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1044 days.

Signed and Sealed this

Twenty-sixth Day of October, 2010

David J. Kappos
*Director of the United States Patent and Trademark Office*